United States Patent
Shen et al.

(10) Patent No.: US 11,972,583 B2
(45) Date of Patent: Apr. 30, 2024

(54) FLUORESCENCE IMAGE REGISTRATION METHOD, GENE SEQUENCING INSTRUMENT, AND STORAGE MEDIUM

(71) Applicant: BGI SHENZHEN, Shenzhen (CN)

(72) Inventors: Jin-Jin Shen, Shenzhen (CN); Da-Wei Li, Shenzhen (CN); Yang-Bao Liu, Shenzhen (CN); Ge Feng, Shenzhen (CN); Mei Li, Shenzhen (CN); Yu-Xiang Li, Shenzhen (CN)

(73) Assignee: BGI SHENZHEN, Shenzhen (CN)

( * ) Notice: Subject to any disclaimer, the term of this patent is extended or adjusted under 35 U.S.C. 154(b) by 409 days.

(21) Appl. No.: 17/426,885

(22) PCT Filed: Jan. 31, 2019

(86) PCT No.: PCT/CN2019/074244
§ 371 (c)(1),
(2) Date: Jul. 29, 2021

(87) PCT Pub. No.: WO2020/155043
PCT Pub. Date: Aug. 6, 2020

(65) Prior Publication Data
US 2022/0108462 A1 Apr. 7, 2022

(51) Int. Cl.
*G06T 7/33* (2017.01)
*C12Q 1/6869* (2018.01)
(Continued)

(52) U.S. Cl.
CPC ............ *G06T 7/337* (2017.01); *C12Q 1/6869* (2013.01); *G01N 21/6458* (2013.01); *G01N 21/6486* (2013.01); *G06T 7/66* (2017.01); *G06T 7/73* (2017.01); *G06T 2207/10064* (2013.01); *G06T 2207/30072* (2013.01); *G06T 2207/30168* (2013.01)

(58) Field of Classification Search
CPC . G06T 7/337; G06T 7/66; G06T 2207/10064; G06T 2207/30072; G06T 2207/30168; C12Q 1/6869; G01N 21/6458; G01N 21/6486
See application file for complete search history.

(56) References Cited

U.S. PATENT DOCUMENTS 10,936,871 B2 * 3/2021 Tran ...................... G06F 3/0346
2011/0256631 A1 * 10/2011 Tomaney ............ C12Q 1/6874
706/12

* cited by examiner

*Primary Examiner* — Diane D Mizrahi
(74) *Attorney, Agent, or Firm* — ScienBiziP, P.C.

(57) ABSTRACT

The present disclosure provides a fluorescence image registration method, the method includes: acquiring a fluorescence image of a biochip; selecting a preset local region of the fluorescence image; acquiring a position of a minimum value of a sum of brightness values of pixels in a first direction and a second direction, and obtaining pixel-level registration points; dividing the pixel-level registration points into non-defective pixels and defective pixels; if the fluorescence image meets the preset standard, correcting positions of the defective pixels according to positions of the non-defective pixels; acquiring a position of a center of gravity of image points of fluorescent molecules according to a center of gravity method; fitting straight lines in the first direction and the second direction respectively according to the position of the center of gravity; and acquiring boundary points of the fluorescence image and calculating the positions of the boundary points.

15 Claims, 11 Drawing Sheets

(51) Int. Cl.
*G01N 21/64* (2006.01)
*G06T 7/66* (2017.01)
*G06T 7/73* (2017.01)

FLUORESCENCE IMAGE REGISTRATION METHOD, GENE SEQUENCING INSTRUMENT, AND STORAGE MEDIUM

FIELD

The disclosure relates to a field of gene sequencing, and in particular to a fluorescence image registration method, a gene sequencing instrument, a gene sequencing system, and a storage medium.

BACKGROUND TECHNIQUE

This section provides background or context for the implementation of the embodiments of the present disclosure stated in the claims and the detailed description. The description here is not to be recognized as prior art just because it is included in this section.

Gene sequencing is analyzing base sequence of specified DNA fragments, namely how the adenine (A), thymine (T), cytosine (C) and guanine (G) bases are arranged. One of the commonly used sequencing methods at present is: the above-mentioned four bases carry four different fluorescent molecules, and different fluorescent molecules emit fluorescence of different wavelengths (colors) after being excited. By identifying the wavelength, the type of the base can be determined, such that the base sequence can be obtained. The second-generation sequencing technology uses a high-resolution microscopy imaging system to take images and collect fluorescence images of DNA nanoballs (i.e., DNB) on a biochip (a gene sequencing chip), and send the fluorescence images to a base recognition software for decoding image signal and obtaining the base sequence. Different fluorescent dyes on abase produces fluorescent molecular signals of different wavelengths. To detect the type of base, it is necessary to analyze fluorescent molecule energy of the base in different scenes, and first locate same position coordinates in different scenes. This is the work of a registration algorithm.

With the development of the second-generation sequencing technology, sequencer products are equipped with software for real-time processing and analysis sequencing data, most of which are equipped with registration and positioning algorithms. First, a base signal corresponds to a specified position in the image. It is necessary to match the corresponding position of the base in the image. Therefore, speed, accuracy and robustness of matching are basic requirements in the image registration. However, the existing image registration algorithms are generally designed based on the CPU, which is low in efficiency. As a throughput of the sequencer increases, a processing time for an image increases linearly, and the requirement of sequencing while synthesizing of the second-generation sequencer may not be guaranteed. Further, the registration of other points of the algorithm depends on the best point extracted. If the best point is not correctly located, the registration quality of all points will be affected. Therefore, there is an urgent need to provide a higher performance image registration method.

SUMMARY OF THE INVENTION

In view of this, it is necessary to provide a fluorescence image registration method, a gene sequencing instrument, a gene sequencing system and a storage median, which can optimize the positioning and registration operation of the fluorescent molecules in the fluorescence image.

A first aspect of the embodiments of the present disclosure provides a fluorescence image registration method, which is applied to a biochip, and the fluorescence image registration method includes:

S1: obtaining at least one fluorescence image of a biochip;

S2: selecting a preset local region of the fluorescence image, the preset local region having at least one borderline frame in the first direction and the second direction, the borderline frame comprising a plurality of image points of fluorescent molecules, and the first direction being perpendicular to the second direction;

S3: acquiring, in the preset local region, a position of a minimum value of a sum of brightness values of pixels in the first direction and the second direction, and acquiring pixel-level registration points according to the position of the minimum value of the sum of brightness values of pixels;

S4: dividing the pixel-level registration points into non-defective pixels and defective pixels according to a preset classification rule;

S5: determining whether the fluorescence image meets a preset standard according to a number of the non-defective pixels, if the fluorescence image meeting the preset standard, goes to block S6; and reobtaining the fluorescence image if the fluorescence image being not meet the preset standard;

S6: correcting positions of the defective pixels according to positions of the non-defective pixels;

S7: detecting image points of fluorescent molecules on a cross line where the pixel-level registration points are located, of borderline frames in the first direction and the second direction, and acquiring a position of a center of gravity of image points of fluorescent molecules according to a center of gravity method;

S8: fitting straight lines in the first direction and the second direction respectively according to the position of the center of gravity of the image points of fluorescent molecules, a cross point of the straight line fitted in the first direction and the straight line fitted in the second direction being a sub-pixel level position of the registration point;

S9: acquiring boundary points of the fluorescence image according to the straight lines fitted in the first direction and the second direction, and calculating positions of the boundary points.

Further, in the above fluorescence image registration method provided by the embodiment of the present disclosure, before obtaining the position of the minimum vale of the sum of brightness values of pixels, the method further comprises:

Obtaining apposition of each template borderline frame in the first direction and the second direction, the template borderline frame is a template line frame preset on the biochip;

Selecting a preset rectangular area according to the position of each template borderline frame; and Obtaining the position of the minimum value of the sum of brightness values of pixels in the first direction and the second direction of the preset rectangular area.

Further, in the above fluorescence image registration method provided by the embodiment of the present disclosure, the acquiring the position of the minimum value of the sum of brightness values of pixels in the first direction and the second direction comprises:

Selecting a plurality of template lines;

Respectively in the first direction and the second direction, sequentially translating the plurality of template lines in a preset rectangular area; and Calculating a superimposed sum of brightness values of the pixels covered by the positions of the plurality of template lines on the preset rectangular area, the superimposed sum of the brightness values being a sum of brightness values of pixels covered by the plurality of template lines.

Further, in the above fluorescence image registration method provided by the embodiment of the present disclosure, the dividing the pixel registration points into non-defective pixels and defective pixels according to the preset classification rule comprises:

Obtaining pixel-level registration points on any column in the first direction of the preset local region;

Calculating an absolute value of a difference in abscissa between one of the pixel-level registration points and each of other pixel-level registration points on the any column; and Determining that a pixel-level registration point is non-defective pixel if there are at least two of the absolute values less than a preset threshold.

Further, in the above fluorescence image registration method provided by the embodiment of the present disclosure, the dividing the pixel registration points into non-defective pixels and defective pixels according to the preset classification rule further comprises:

Obtaining, in the second direction of the preset local region, the pixel registration points on any row;

Selecting one of the obtained pixel-level registration points, and obtaining a plurality of slopes by calculating a slope between the selected pixel-level registration point and each of other pixel-level registration points on the any row;

Sorting the plurality of slopes according to a preset sorting rule, obtaining a first median value from the plurality of slopes and setting the first median value as a first slope of the selected pixel-level registration point:

Obtaining a first slope of each of the other pixel-level registration points on the any row, and sorting all the first slopes of the pixel-level registration points on the any row according to the preset sorting rule, obtaining a second median value from all the first slopes and setting the second median as a second slope of the any row; and setting a point corresponding to the second slope on the any row as a reference point;

Obtaining a second slope of each of other rows, and sorting the second slopes of all rows of the preset local region according to the preset sorting rule, and obtaining a third median value from all the second slopes and setting the third median value as a common slope of all rows; and Performing a straight line fitting for all rows according to the common slope and the reference point, and dividing the pixel-level registration points into non-defective pixels and defective pixels according to the fitted straight line.

Further, in the above fluorescence image registration method provided by the embodiment of the present disclosure, the correcting the positions of the defective pixels according to the positions of the non-defective pixels comprises:

Obtaining a mean value of the abscissas of the non-defective pixels in the first direction of the preset local region, and assigning the mean value of the abscissas to the defective pixels;

Obtaining, in the second direction of the preset local region, the abscissa of the defective pixel, and correcting the ordinate of the defective pixel according to the fitted straight line.

Further, in the above fluorescence image registration method provided by the embodiment of the present disclosure, the acquiring the position of the center of gravity of imagepointsoffluorescentmoleculesaccordingtothecenterof-gravitymethodcomprises:

Acquiring position coordinates of the pixel-level registration points;

Acquiring brightness values of pixels of the image points of fluorescent molecules;

Acquiring the position of the center of gravity of image points of the fluorescent molecules according to a preset center of gravity formula.

A second aspect of the embodiments of the present disclosure provides a gene sequencing system applied to a biochip, wherein the gene sequencing system comprises:

A fluorescence image acquisition module being used to obtain at least one fluorescence image of a biochip;

A local region acquisition module being used to select a preset local region of the fluorescence image, the preset local region having at least one borderline frame in the first direction and the second direction, the borderline frame comprising a plurality of image points of fluorescent molecules, and the first direction being perpendicular to the second direction;

A pixel-level registration point acquisition module being used to acquire, in the preset local region, a position of a minimum value of a sum of brightness values of pixels in the first direction and the second direction, and acquire pixel-level registration points according to the position of the minimum value of the sum of brightness values of pixels;

A registration point classification module being used to divide the pixel-level registration points into non-defective pixels and defective pixels according to a preset classification rule;

An image quality judgment module being used to determine whether the fluorescence image meets a preset standard according to a number of the non-defective pixels:

A position correction module being used to correct the positions of the defective pixels according to the positions of the non-defective pixels;

A gravity center acquisition module being used to detect image points of the fluorescent molecules on a cross line where the pixel-level registration points are located, of the borderline frames in the first direction and the second direction, and acquire a position of a center of gravity of image points of fluorescent molecules according to a center of gravity method;

A sub-pixel level registration point acquisition module being used to fit straight lines in the first direction and the second direction respectively according to the position of the center of gravity of the image points of fluorescent molecules, a cross point of the straight line fitted in the first direction and the straight line fitted in the second direction being a sub-pixel level position of the registration point; and A boundary point position acquisition module being used to acquire boundary points of the fluorescence image according to the straight lines fitted in the first direction and the second direction, and calculate positions of the boundary points.

A third aspect of the embodiments of the present disclosure provides a gene sequencing instrument, wherein the gene sequencing instrument comprises a processor and the processor is used to implement the fluorescence image registration method when executing a computer program stored in a storage device.

A fourth aspect of the embodiments of the present disclosure provides a non-volatile computer-readable storage medium with a computer program stored thereon, wherein the computer program is executed by a processor to implement the fluorescence image registration method.

The fluorescence image registration method, the gene sequencing instrument the gene sequencing system and the storage medium provided by the embodiments of the present disclosure can obtain at least one fluorescence image of a biochip; select a preset local region of the fluorescence image, the preset local region having at least one borderline frame in the first direction and the second direction, the borderline frame comprising a plurality of image points of fluorescent molecules, and the first direction being perpendicular to the second direction; acquire, in the preset local region, a position of a minimum value of a sum of brightness values of pixels in the first direction and the second direction, and acquire pixel-level registration points according to the position of the minimum value of the sum of brightness values of pixels; divide the pixel-level registration points into non-defective pixels and defective pixels according to a preset classification rule; determine whether the fluorescence image meets a preset standard according to a number of the non-defective pixels, if it is determined that the fluorescence image meets the preset standard, correcting the positions of the defective pixels according to the positions of the non-defective pixels; detect image points of the fluorescent molecules on a cross line where the pixel-level registration points are located, of the borderline frames in the first direction and the second direction, and acquire a position of a center of gravity of image points of fluorescent molecules according to a center of gravity method; fit straight lines in the first direction and the second direction respectively according to the position of the center of gravity of the image points of fluorescent molecules, a cross point of the straight line fitted in the first direction and the straight line fitted in the second direction being a sub-pixel level position of the registration point; acquiring boundary points of the fluorescence image according to the straight lines fitted in the first direction and the second direction, and calculating positions of the boundary points. The present disclosure provides a high-precision GPU parallel registration fluorescent image based on point features, which can locate and register base information images of different sequencing platforms with high accuracy and efficiency. The fluorescence image registration method provided by the embodiment of the present disclosure also determines whether the quality of the fluorescence image meets the standard by the number of non-defective pixels, and discards the fluorescence image that does not meet the standard, so it has a strong anti-impurity interference ability.

SYMBOL DESCRIPTION OF MAIN COMPONENTS

Figure 1:
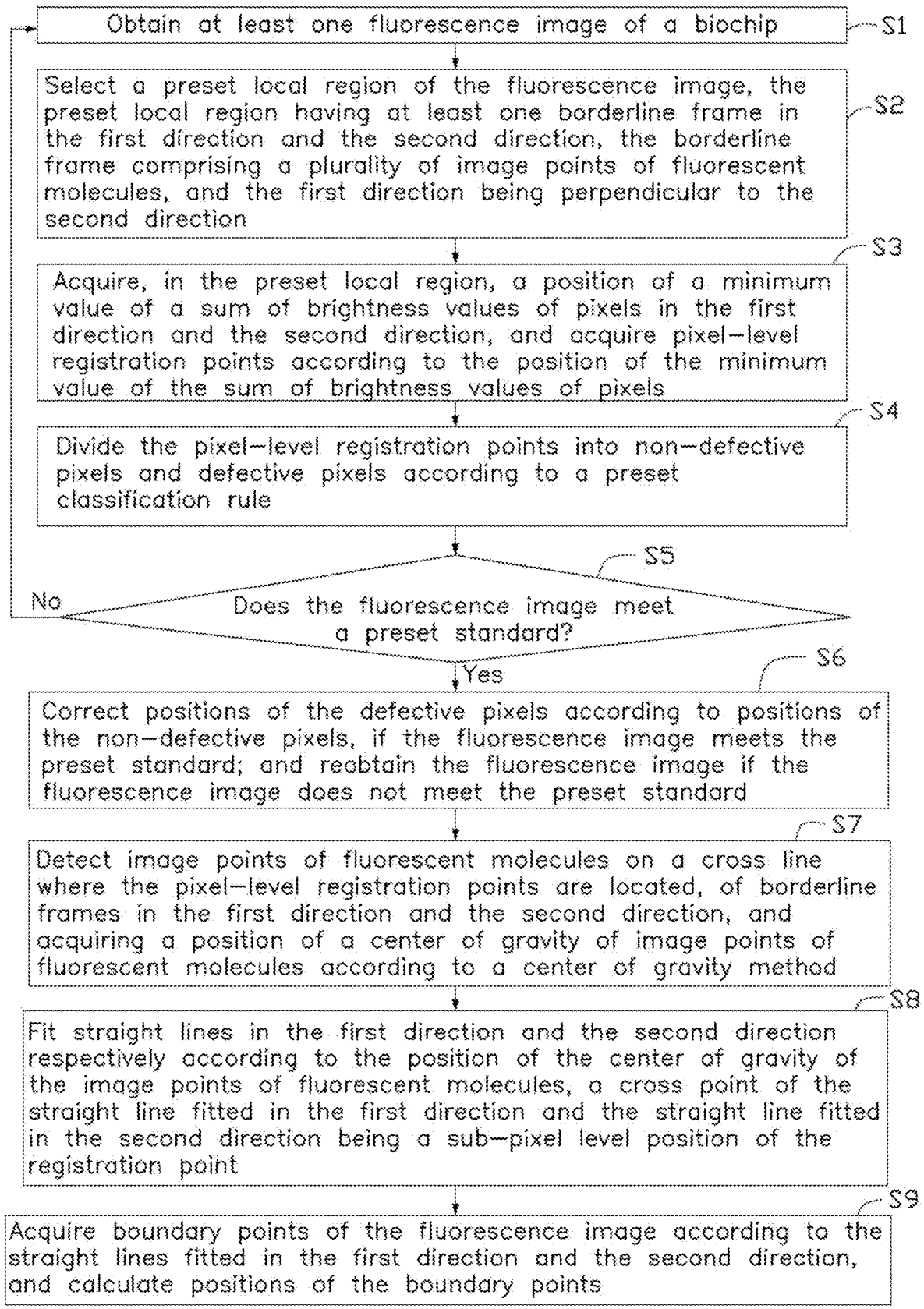
FIG. 1 is a flowchart of a fluorescence image registration method according to an embodiment of the present disclosure.

Gene sequencing instrument 1
Storage device 10
Display screen 20
processor 30
Gene sequencing system 100
Fluorescence image acquisition module 101
Local region acquisition module 103
Pixel-level registration point acquisition module 105
Registration point classification module 107
Image quality judgment module 109
Position correction module 111
Gravity center acquisition module 113
Sub-pixel level registration point acquisition module 115
Boundary point position acquisition module 117

The following specified implementations will further illustrate the embodiments of the present disclosure in conjunction with the above-mentioned drawings.

DETAILED DESCRIPTION

In order to be able to understand the object, features and advantages of die embodiments of the present disclosure, implementations of the disclosure will now be described, by way of embodiments only, with reference to the drawings. It should be noted that non-conflicting details and features in the embodiments of the present disclosure may be combined with each other.

In the following description, specific details are explained in order to make the embodiments of the present disclosure understandable. The described embodiments me only a portion of, rather than all of the embodiments of the present disclosure of them. Based on the embodiments of the present disclosure, other embodiments obtained by a person of ordinary skill in the art without creative work shall be within the scope of the present disclosure.

Unless otherwise defined, all technical terms used herein have the same meaning as commonly understood by one of ordinary skill in the art. The technical terms used herein are not to be considered as limiting the scope of the embodiments.

To understand part of the content of the present disclosure, please refer to US Patent U.S. Pat. No. 9,880,089 and its family patents, but these content are not the technical solutions claimed by the present disclosure, so the technical content will not be explained repeatedly in the text.

FIG. 1 is a flowchart of a fluorescence image registration method according to an embodiment of the present disclosure. As shown in FIG. 1, the fluorescence image registration method may include the following blocks:

S1: Acquiring at least one fluorescence image of a biochip.

In this embodiment, the biochip may be a gene sequencing chip, and the fluorescence image may be a fluorescence signal image taken during sequencing. The biochip has a plurality of track lines (also referred to as "Trackline", such as the track region in US Patent U.S. Pat. No. 9,880,089) in a first direction and a second direction, wherein the first direction is perpendicular to the second direction, and the first direction may be a vertical direction, and the second direction may be a horizontal direction. An area formed between two adjacent track lines in the first direction and two adjacent track lines in the second directions is called as a block, the block may be an inner block and an outer block. There is a plurality of sites uniformly distributed in each block on the biochip. The site can adsorb DNA nanosphere molecules (DNB), and the DNA nanosphere molecules can be amplified products including DNA fragments. The DNA nanosphere molecules carry fluorescent molecules during base synthesis, and the fluorescent molecules emit fluorescent signals when excited. The fluorescent molecules can be fixedly arranged on the biochip according to preset rules, and through specified design and processing, some positions of the biochip have no sites, that is, no fluorescent molecules exist. When the fluorescent molecules of more than 25% (adenine (A), thymine (T), cytosine (C) and guanine (G) are balanced) at random positions emits light, a non-luminous border line frame is highlighted. The highlighted borderline frame may be composed of three image points of fluorescent molecules, image points of fluorescent molecules in a middle row are bright spots, and image points of fluorescent molecules on both sides of the middle row are not bright. Image points of fluorescent molecules in the middle row form track lines, and image points of fluorescent molecules on both sides of the middle row form dark lines. The points of the fluorescent molecules that images are defined to be image points of fluorescent molecules. It can be understood that the borderline frame may include the track line and the dark lines on both sides of the track line.

During a sequencing process, a TDI camera can be used to scan the biochip according to a preset scanning order to acquire the fluorescence image. The preset scanning order may be preset by a terminal user, and the preset scanning order includes, but is not limited to scanning in a top-down order.

S2: Selecting a preset local region of the fluorescence image, the preset local region having at least one borderline frame in the first direction and the second direction, the borderline frame comprising a plurality of image points of fluorescent molecules, the first direction being perpendicular to the second direction.

In this embodiment, the preset local region may be preset by the terminal user the preset local region having at least one borderline frame in the first direction and the second direction, that is, at least one registration point exists in the preset local region.

Figure 2:
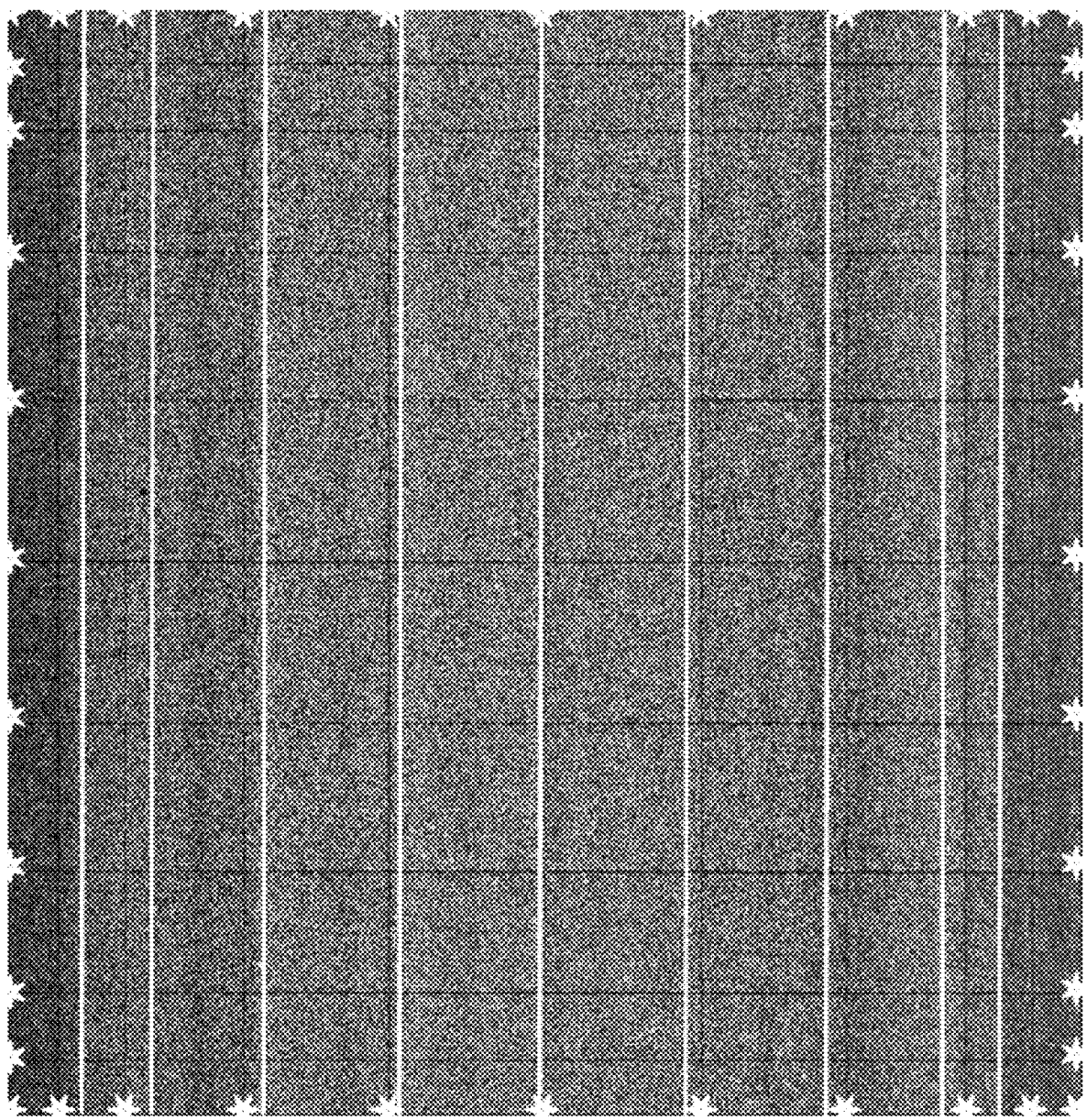
FIG. 2 is a schematic diagram of a preset local region of a fluorescence image provided by an embodiment of the present disclosure.

Please refer to FIG. 2, which is a schematic diagram of a preset local region of a fluorescence image provided by an embodiment of the present disclosure. As shown in FIG. 2, the preset local region may be a 9*9 area, in which there are 9 borderline frames in the first direction (indicated by the black solid line in FIG. 2), and there are 9 borderline frames (represented by black solid lines in FIG. 2) in the second direction. The borderline frames in the first direction intersect the borderline frames in the second direction, and 81 (9*9) cross points (registration points) are obtained. The white solid line in FIG. 2 represents a template borderline frame, and the template borderline frame is a template line frame preset on the biochip. There are locations marked with asterisks on the four boundaries in FIG. 2, and the locations marked with white asterisks are positions of boundary points of the fluorescence image.

S3: Acquiring, in the preset local region, a position of a minimum value of a sum of brightness values of pixels in the first direction and the second direction, and acquiring pixel-level registration points according to the position of the minimum value of the sum of brightness values of pixels.

In this embodiment, before obtaining the position of the minimum value of the sum of brightness values of pixels, the method further includes: obtaining a position of each template borderline frame in the first direction and the second direction. The template borderline frame is a template line frame preset on the biochip, which is an actual physical position of the borderline frame of the biochip. Because the camera imaging produces distortion, so there will be a deviation between the borderline frame of the fluorescence signal image and the template borderline frame. The method further includes: selecting a preset rectangular area according to the position of each template borderline frame; obtaining the position of the minimum value of the sum of brightness values of pixels in the first direction and the second direction of the preset rectangular area. Wherein, the preset rectangular area is preset by the terminal user. According to the position of the template borderline frame in the first direction and the second direction, the position of the template registration point in the preset local region can be obtained. The preset rectangular area includes a template registration point. Preferably, the preset rectangular area may be arranged symmetrically relative to the position of the template registration point. It is understandable that, for a certain column in the first direction, a preset rectangular area needs to be selected at the position of the template borderline frame where each template registration point on the column is located, and the position of the minimum value of the sum of brightness values of pixels in the first direction of each preset rectangular area is obtained, so as to obtain the position of the actual borderline frame on a column in a longitudinal direction.

Figure 3A:
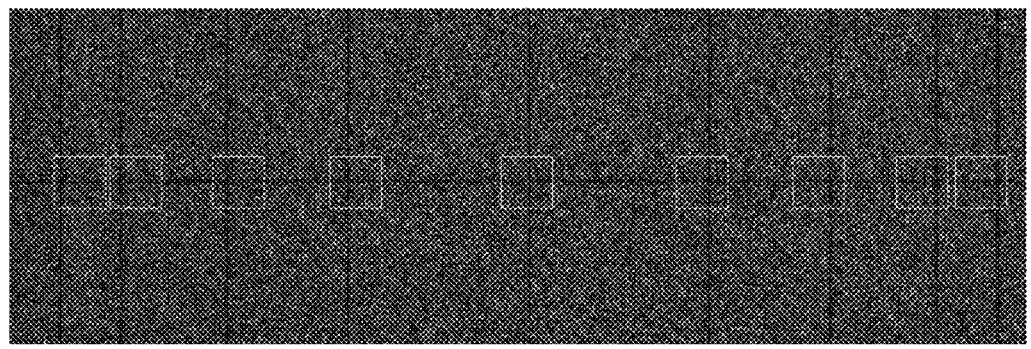
FIG. 3A is a schematic diagram of pixel-level positioning of a borderline frame in a second direction.
Figure 3B:
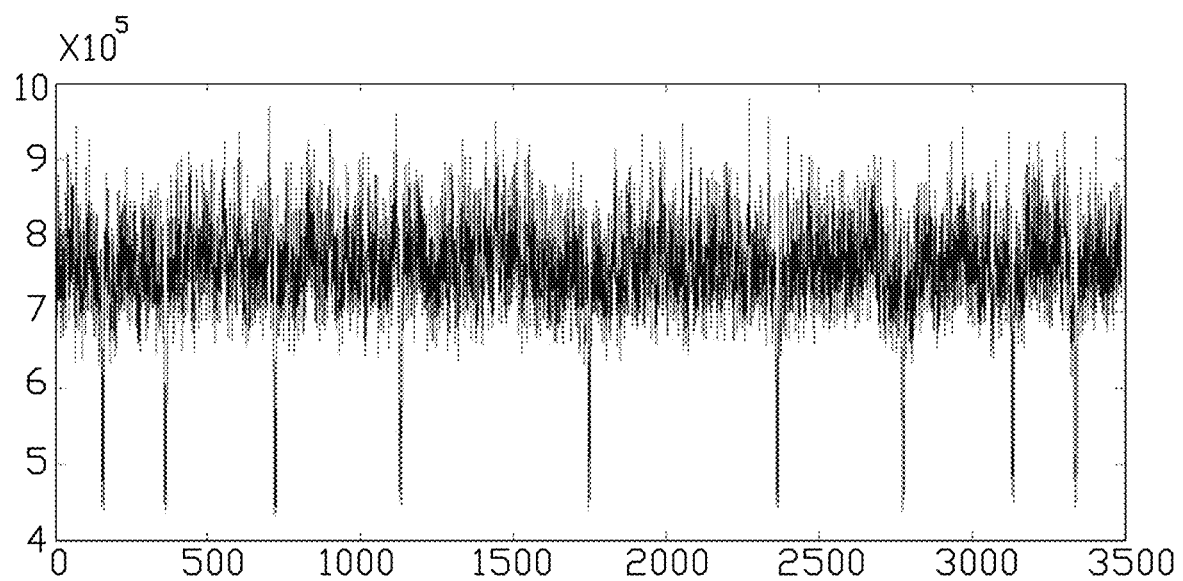
FIG. 3B is a curve diagram of a sum of brightness values of pixels of a preset rectangular area in the second direction.

Please refer to FIG. 3A and FIG. 3B, FIG. 3A is a schematic diagram of pixel-level positioning of the borderline frame in the second direction, and FIG. 3B is a curve diagram of the sum of brightness values of pixels of a preset rectangular area in the second direction. As shown in FIG. 3A, there are two types of borderline frames in the figure, black represents the actual borderline frame, and white represents the template borderline frame. Taking the second direction as an example, the position of the template borderline frame in the second direction is obtained, and a preset rectangular area is selected according to the position of the template borderline frame. There is a preset rectangular area at the position of each template borderline frame in FIG. 3A (the preset rectangular area is represented by a white solid line), and a center of the preset rectangular area is generally the cross point of the template borderline frame in the first direction and the template borderline frame in the second direction. In order to avoid overlapping of borderline frames that are searched when obtaining the position of the minimum value of the sum of brightness values of pixels in the first direction and the second direction, a length and a width of the preset rectangular area cannot be greater than a shortest distance of the template borderline frame. When an area of the preset rectangular area is set to be large, it will affect a running speed of a program; when the area of the preset rectangular area is set to be small, it will affect an positioning accuracy of positioning the dark line. Therefore, in this embodiment, the size of the preset rectangular area is set to 128*128 pixels, which can simultaneously ensure the running speed and the positioning accuracy of the program.

The acquiring the position of the minimum value of the sum of brightness values of pixels in the first direction and the second direction includes: selecting a plurality of template lines; respectively in the first direction and the second direction, sequentially translating the plurality of template lines in the preset rectangular area; calculating a superimposed sum of the brightness values of the pixels covered by the positions of the plurality of template lines on the preset rectangular area, and the superimposed sum of de brightness values is the sum of brightness values of pixels covered by the plurality of template lines. The acquiring the pixel-level registration points according to the position of the minimum value of the sum of brightness values of pixels includes: determining tat the cross point of the position of the minimum value of the sum of brightness values of pixels in the first direction and the position of the minimum value of the sum of brightness values of pixels in the second direction is the pixel-level registration point. As shown in FIG. 3B, the sum of the brightness values of all pixels facing the position of the borderline frame is kept to the lowest value, and the borderline frame in FIG. 3B shows obvious wave troughs. Each trough in FIG. 3B corresponds to the position of the borderline frame in FIG. 3A.

Figure 4A:
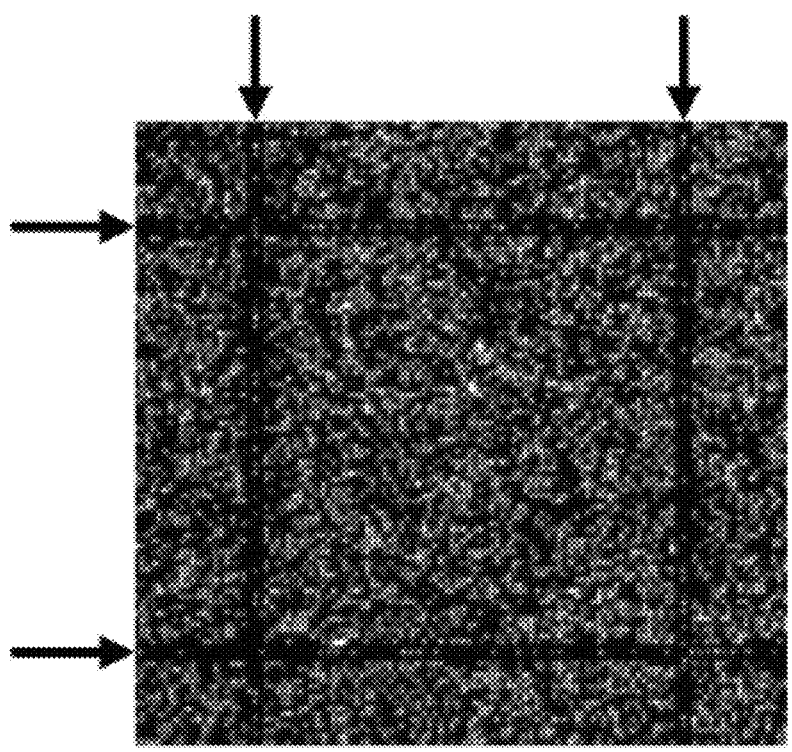
FIG. 4A is an enlarged view of a partial of the borderline frame in the fluorescence image.
Figure 4B:
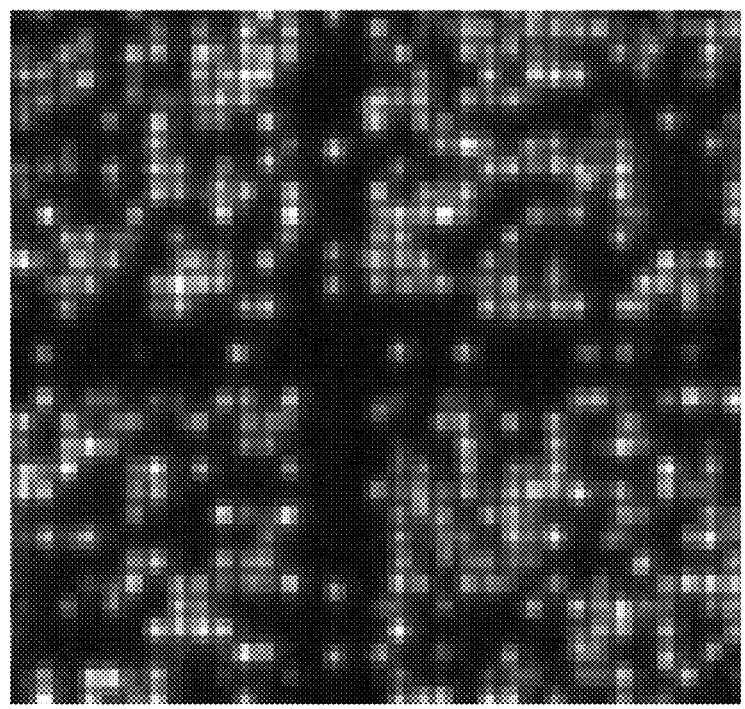
FIG. 4B is a schematic diagram of an arrangement of image points of fluorescent molecules on the borderline frame shown in FIG. 4A.
Figure 4C:
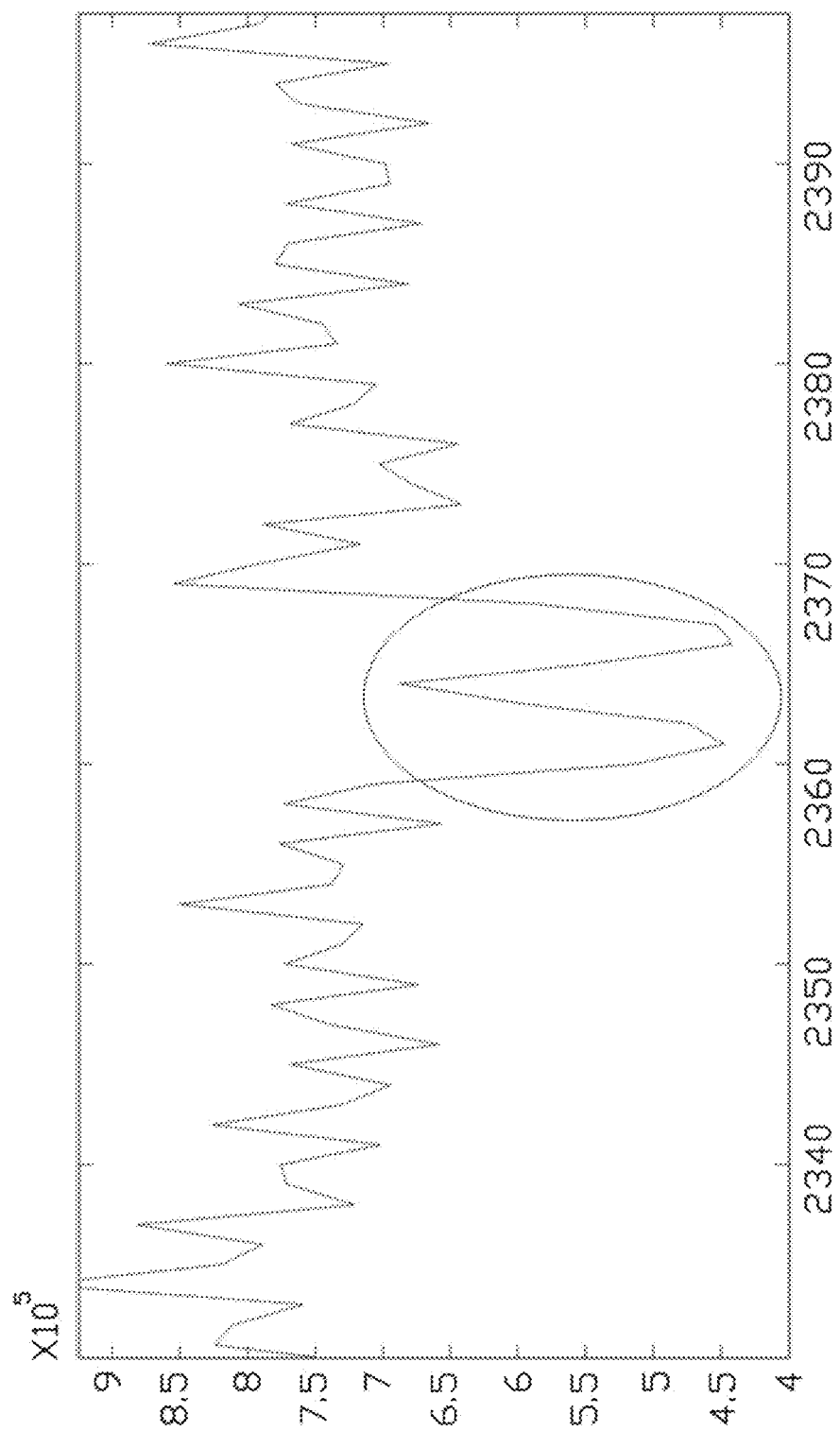
FIG. 4C is a schematic diagram of features of a sum of brightness values of pixels in the preset local region.

Please refer to FIG. 4A, FIG. 4B, and FIG. 4C. FIG. 4A is an enlarged view of part of the borderline frame in the fluorescence image. FIG. 4B is a schematic diagram of the arrangement of image points of fluorescent molecules on the borderline frame shown in FIG. 4A. As shown in FIG. 4A and FIG. 4B, in FIG. 4A, there are two borderline frames in the first direction and the second direction respectively (the position pointed by the arrow is the position where the borderline frame is located), which highlights the borderline frame can be composed of three image points of fluorescent molecules, image points of fluorescent molecules in the middle row are bright spots, and image points of fluorescent molecules on both sides of the middle row are not bright. Image points of fluorescent molecules in the middle row form a track line, and image points of fluorescent molecules on both sides of the middle row form dark lines. It can be understood that the highlighted borderline frame may include the track line and dark lines on both sides of the track line. It is understandable that the size of the fluorescent molecules corresponding to different biochips and different cameras is different. The present disclosure takes the size of 3*3 pixels as an example. As shown in FIG. 4C, the W-shaped line feature (The part selected by the black ellipse), there are two troughs and one wave crest in the W-shaped line feature. It is understandable that the positions of the two troughs are the positions corresponding to the dark lines on both sides of the track line on the biochip, and the brightness values of pixels of the positions corresponding to the dark lines are lower. The position corresponding to the wave crest in the W-shaped line feature is the position corresponding to the track line, and the brightness values of pixels of the position corresponding to the track line are higher. According to this feature, the pixels at the positions (−4)(−3)(−2) and (2)(3)(4) on both sides of each point in the preset rectangular area are summed, and the sum is the smallest point corresponds to the position of the borderline frame. Using the same method, the position of the borderline frame in the first direction can be obtained. The cross point of each borderline frame in the first direction and each borderline frame in the second direction is the pixel-level registration point, that is, 81 (9*9) pieces in total.

S4: Dividing the pixel-level registration points into non-defective pixels and defective pixels according to a preset classification rule.

In this embodiment, after pixel-level registration points are obtained, it is necessary to perform non-defective or defective pixel determination and correction for each pixel-level registration point. The embodiment of the present disclosure provides a straight line fitting method to determine the quality of each pixel-level registration point, and at fie same time correct the defective pixels, that is, correct while judging. Finally, all the pixel-level registration points are combined to determine a quality of the fluorescence image. The specified process is as follows:

The dividing the pixel registration points into non-defective pixels and defective pixels according to the preset classification rule includes: obtaining the pixel-level registration points on any column in the first direction of the preset local region; calculating an absolute value of a difference in abscissa between one of the pixel-level registration points and each of other pixel-level registration points on the any column; if there are at least two absolute values less than a preset threshold, it is determined that the pixel-level registration point is non-defective pixel, otherwise, the pixel-level registration point is determined to be a defective pixel. The preset threshold may be preset by those skilled in the art according to their experience. In this embodiment, a range of searching for fluorescent molecules near the borderline frame is 3 pixels during sub-pixel level registration. As long as it is within 3 pixels, a best position can be located through sub-pixel registration. Therefore, the preset threshold is 3 pixels.

In the second direction of the preset local region, obtaining the pixel registration points on any row; selecting one of the obtained pixel-level registration points and obtaining a plurality of slopes by calculating a slope between the selected pixel-level registration point and each of other pixel-level registration points on the any row; sorting the plurality of slopes according to a preset sorting rule (the preset sorting order can be from small to large, or from large to small), obtaining a first median value from the plurality of slopes and setting the first median value as a first slope of the selected pixel-level registration point; obtaining a first slope of each of the other pixel-level registration points on the any row, and sorting all the first slopes of the pixel-level registration points on be any row according to the preset sorting rule, obtaining a second median value from all the first slopes and setting the second median as a second slope of the any row, and setting a point corresponding to the second slope on the any row as a reference point; and obtaining a second slope of each of other rows, and sorting the second slopes of all rows of the preset local region according to the preset sorting rule, and obtaining a third median value from all the second slopes and setting the third median value as a common slope of all rows; performing a straight line fitting for all rows according to the common slope and the reference point, and dividing the pixel-level registration points into non-defective pixels and defective pixels according to the fitted straight line. Specially, when a distance between the registration point and the straight line in the first direction is greater than 3 pixels, it is determined that the registration point is a defective pixel. That is, because the pixel-level abscissa of borderline frame (track line) of the first direction has been previously determined, the ordinate corresponding to the line in second direction (slope) can be obtained according to the abscissa, and then obtaining absolute value by calculating a difference between the pixel-level registration point and the ordinate. If the absolute value is greater than 3 pixels, then the registration point is determined to be a defective pixel.

S5: Determining whether the fluorescence image meets a preset stand and according to a number of the non-defective pixels. If it is determined that the fluorescence image meets the preset standard, the process goes to block S6, if it is determined that the fluorescence image does not meet the preset standard, the process returns block S1, and re-acquires a next fluorescence image.

In this embodiment, the determining of whether the fluorescence image meets the preset standard according to the number of the non-defective pixels includes: in the first direction, if the number of non-defective pixels in each column is greater than 3, then determining that the fluorescence image meets the preset standard, otherwise, the fluorescence image is discarded. In the second direction, if the number of non-defective pixels on each line is greater than a preset number, it is determined that the fluorescence image meets the preset standard, otherwise, the fluorescence image is discarded, and block S1 is executed to select the next fluorescence image. The preset number is pre-adjusted and set according to a size of the preset local region. In this embodiment, the preset local region is a 9*9 area, and the preset number is 5. That is, in the second direction, if the number of non-defective pixels on each line is greater than 5, it is determined that the fluorescence image meets the preset standard, otherwise, the fluorescence image is discarded.

S6: Correcting the positions of the defective pixels according to the positions of the non-defective pixels.

In this embodiment, taking a TDI camera to scan the biochip in a top-down scanning order to obtain the fluorescence image as an example, the borderline frame in the first direction always maintains a vertical orientation due to optical characteristics of a TDI mode. Therefore, the defective pixels in the first direction may be corrected first, and the correction of the defective pixels in the second direction depends on the abscissa of the corrected defective pixel in the first direction.

The correcting the positions of the defective pixels according to the positions of the non-defective pixels includes: obtaining a mean value of the abscissas of the non-defective pixels in the first direction of the preset local region, and assigning the mean value of the abscissas to the defective pixels; in the second direction of the preset local region, obtaining the abscissa of the defective pixel, and correcting the ordinate of the defective pixel according to the fitted straight line. It is understandable that after correcting the defective pixels in the first direction of the preset local region, the abscissa of the pixel-level registration point can be determined. Therefore, in the second direction of the preset local region, the ordinate of the defective pixel can be corrected by the fitted straight line according to the determined abscissa of the defective pixel.

Figure 5A:
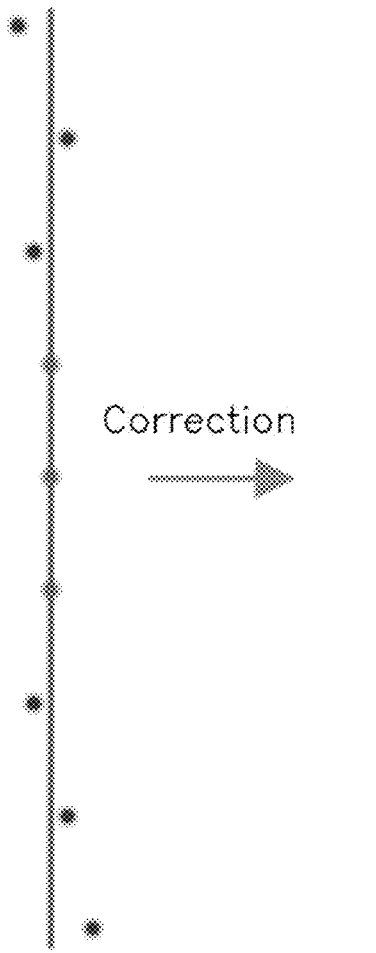
FIG. 5A is a schematic diagram of pixel-level correction in a first direction.
Figure 5B:
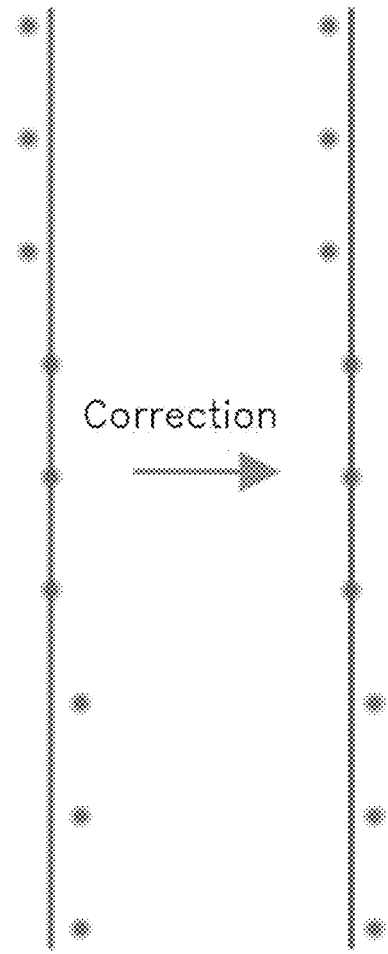
FIG. 5B is a schematic diagram of extreme correction in the first direction.

Please refer to FIG. 5A and FIG. 5B. FIG. 5A is a schematic diagram of pixel-level correction in the first direction, and FIG. 5B is a schematic diagram of extreme correction in the first direction. As shown in FIG. 5A, there are two straight lines in the first direction, the left straight line is a straight line before correction, there are three non-defective pixels on the left straight line (gray solid circles represent non-defective pixels), and there are six defective pixels near the left straight line that need to be corrected (black solid circles represent defective pixels). By obtaining the mean value of the abscissas of the non-defective pixels and assigning the mean value of the abscissas to the defective pixel, the defective pixels can be corrected to obtain the straight line on the right, the straight line on the right is the corrected straight line, and the straight line on the right is present 9 non-defective pixels. It is understandable that there is a more extreme situation. As shown in FIG. 5B, there are 9 pixel-level registration points on the straight line on the left, and every three points are on the same straight line. At this time, according to the above-mentioned non-defective pixel determination method, all 9 points are non-defective pixels. However, these 9 pixel-level registration points are not on the same straight line. Without relying on the template borderline frame, it is impossible to determine which three points are located on the straight line where the borderline frame is located. As shown by the right line, the point distribution before and after correction has not changed. In order to avoid this situation, the method further includes: obtaining a difference in abscissa of any two of the 9 pixel-level registration points; determining whether the difference in abscissa is greater than a preset abscissa threshold, if it is determined that the difference in abscissa is greater than the preset abscissa threshold, the fluorescence image is considered to be of poor quality, and the fluorescence image is discarded.

S7: Detecting image points of the fluorescent molecules on a cross line where the pixel-level registration points are located, of the borderline frames in the first direction and the second direction, and acquiring a position of a center of gravity of image points of fluorescent molecules according to a center of gravity method.

In this embodiment, after obtaining the pixel-level registration points, it is necessary to perform higher-precision positioning of the pixel-level registration points, i.e., sub-pixel-level registration. The acquiring the position of the center of gravity of image points of fluorescent molecules according to the center of gravity method includes: acquiring position coordinates of the pixel-level registration points; acquiring brightness values of pixels of the image points of fluorescent molecules; acquiring the position of the center of gravity of image points of the fluorescent molecules according to a preset center of gravity formula.

Image points of fluorescent molecules on the cross line of the borderline frames are actually coding sites (such as fluorescent spots on the track region in US Patent U.S. Pat. No. 9,880,089) on the track line.

Figure 6A:
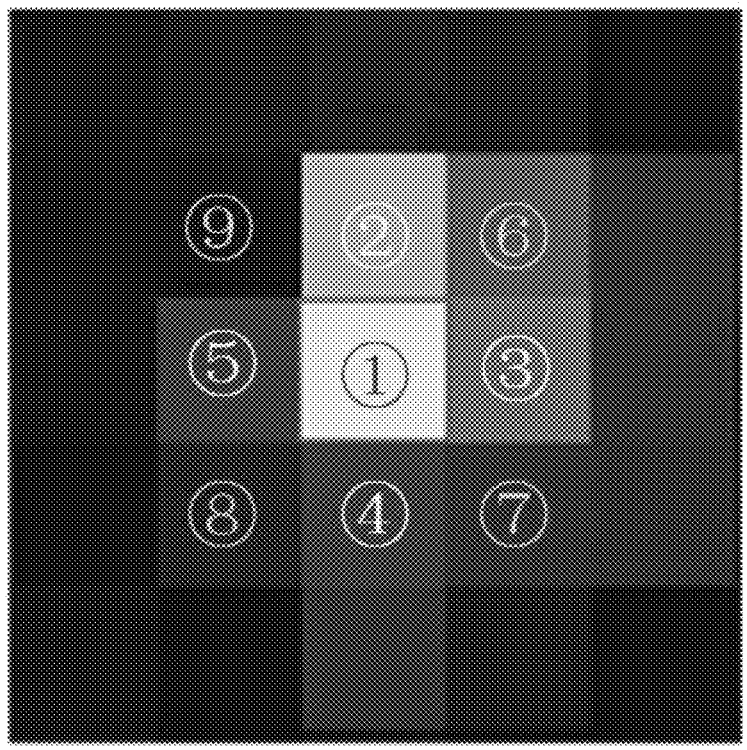
FIG. 6A is a schematic diagram of pixel-level positions.
Figure 6B:
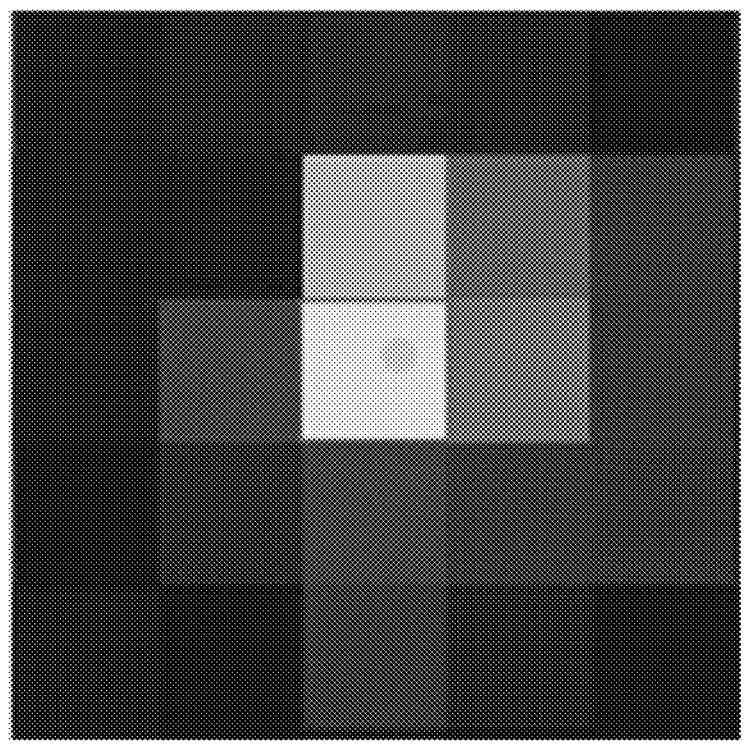
FIG. 6B is a schematic diagram of sub-pixel level positions.

Please refer to FIG. 6A and FIG. 6B. FIG. 6A is a schematic diagram of pixel-level positions, and FIG. 6B is a schematic diagram of sub-pixel-level positions. As shown in FIG. 6A, the black line frame area represents a pixel. If the pixel is further subdivided, sub-pixel position is obtained, as shown in the gray solid circle in FIG. 6B. Detect image points of fluorescent molecules on the cross line where the pixel-level registration point is located. The range of the cross line is set to −64 to 64 pixels, that is, the length is 128 pixels, which is consistent with the length of the preset rectangular area. Detection conditions of image points of fluorescent molecules are shown in FIG. 6A. Within the range of 3*3 pixels, the brightness value of position ① is the highest and greater than the image background value, and the brightness value of each of positions ②③④⑤ is higher than that of ⑥⑦⑧⑨. Then use the center of gravity method to obtain the position of the center of gravity of image points of fluorescent molecules. The formula of the center of gravity method is as follows:

$$X=X_1+(H_3-H_5)/(H_1+H_3+H_5-H_{bg}\times 3)$$

$$Y=Y_1+(H_4-H_2)/(H_1+H_2+H_4-H_{bg}\times 3)$$

In the above formula, $(X_1, Y_1)$ represent pixel-level coordinates of ①, $H_{1\sim 5}$ respectively represent the brightness value of the position corresponding to the number, and $H_{bg}$ represents the image background value.

S8: Fitting straight lines in the first direction and the second direction respectively according to the position of the center of gravity of the image points of fluorescent molecules, a cross point of the straight line fitted in the first direction and the straight line fitted in the second direction being a sub-pixel level position of the registration point.

In this embodiment, according to the acquired position of the center of gravity of image points of fluorescent molecules, a straight line is fitted in the first direction and a straight line is fitted in the second direction by a least square method, the cross point of the straight line fitted in the first direction and the straight line fitted in the second direction is the sub-pixel level position of the registration point.

Figure 7A:
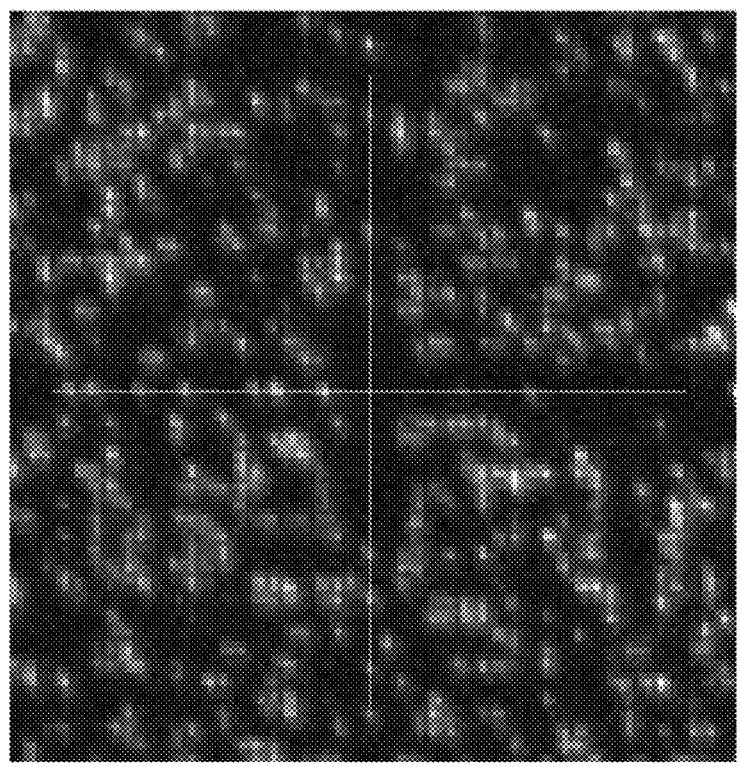
FIG. 7A is a schematic diagram of sub-pixel level registration.
Figure 7B:
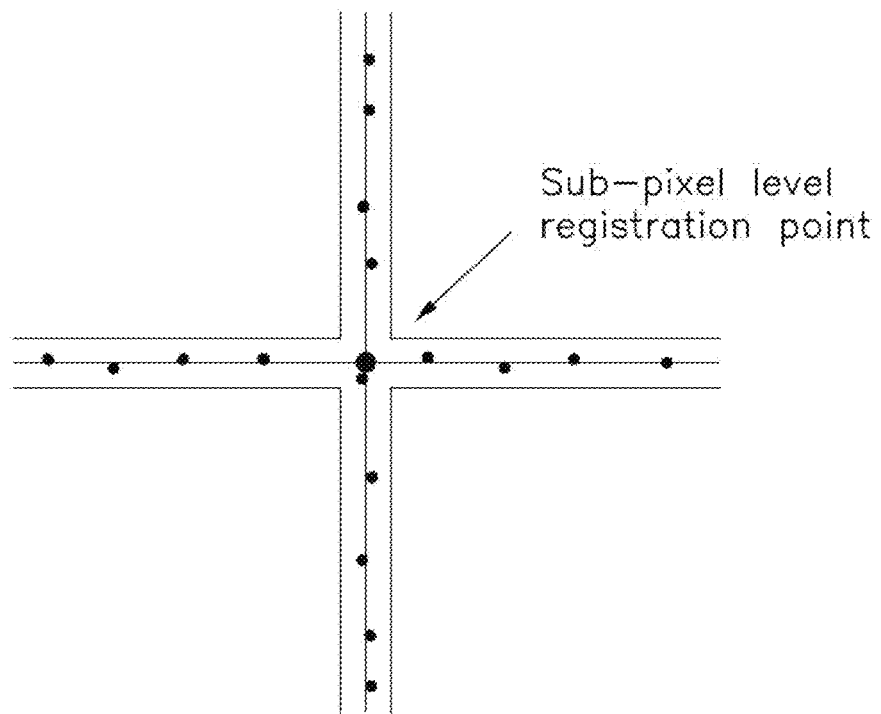
FIG. 7B is another schematic diagram of sub-pixel level registration.

Please refer to FIG. 7A and FIG. 7B. FIG. 7A is a schematic diagram of sub-pixel level registration, and FIG. 7B is another schematic diagram of sub-pixel level registration. The center of gravity of the detected image points of fluorescent molecules is fitted to straight lines in the first direction and the second direction by the least square method, and the crosspoint of the straight lines is the sub-pixel position of the registration point. In FIG. 7B, the black solid circle represents the sub-pixel level registration point, and the gray solid circle represents the center of gravity of image points of fluorescent molecules.

S9: Acquiring boundary points of the fluorescence image according to the straight lines fitted in the first direction and the second direction, and calculating positions of the boundary points.

Please refer to FIG. 2. In FIG. 2, there are positions marked with asterisks on four boundaries. The position marked with asterisks is the position of the boundary point of the fluorescence image. The points on a boundary of the fluorescence image can be calculated according to the straight line fitted when the sub-pixel level registration point is corrected. It is understandable that since a coordinate value of the boundary point is known (for example, the abscissas of the boundary points on the leftmost column are all 0), so another coordinate value of the boundary point can be obtained by substituting e known coordinate value into the fitted straight line. It is understandable that, for an area with a preset local region of 9*9, a total of 121 (11*11) sub-pixel-level registration points can be obtained by the above method.

The embodiment of the present disclosure provides a fluorescence image registration method, the method including obtaining at least one fluorescence image of a biochip; selecting a preset local region of the fluorescence image, the preset local region having at least one borderline frame in the first direction and the second direction, the borderline frame comprising a plurality of image points of fluorescent molecules, and the first direction being perpendicular to the second direction; acquiring, in the preset local region, a position of a minimum value of a sum of brightness values of pixels in the first direction and the second direction, and acquiring pixel-level registration points according to the position of the minimum value of the sum of brightness values of pixels; dividing the pixel-level registration points into non-defective pixels and defective pixels according to a preset classification rule; determining whether the fluorescence image meets a preset standard according to a number of the non-defective pixels, if it is determined that the fluorescence image meets the preset standard, correcting the positions of the defective pixels according to the positions of the non-defective pixels; detecting image points of the fluorescent molecules on a cross line where the pixel-level registration points are located, of the borderline frames in the first direction and the second direction, and acquiring a position of a center of gravity of image points of fluorescent molecules according b a center of gravity method; fitting straight lines in the first direction and the second direction respectively according to the position of the center of gravity of the image points of fluorescent molecules, a cross point of the straight line fitted in the first direction and the straight line fitted in the second direction being a sub-pixel level position of the registration point; acquiring boundary points of the fluorescence image according to the straight lines fitted in the first direction and the second direction, and calculating positions of the boundary points. The present disclosure provides a high-precision GPU parallel registration fluorescent image based on point features, which can locate and register base information images of different sequencing platforms with high accuracy and efficiency. The fluorescence image registration method provided by the embodiment of the present disclosure also determines whether the quality of the fluorescence image meets the standard by the number of non-defective pixels, and discards the fluorescence image that does not meet the standard, so it has a strong anti-impurity interference ability.

Figure 8:
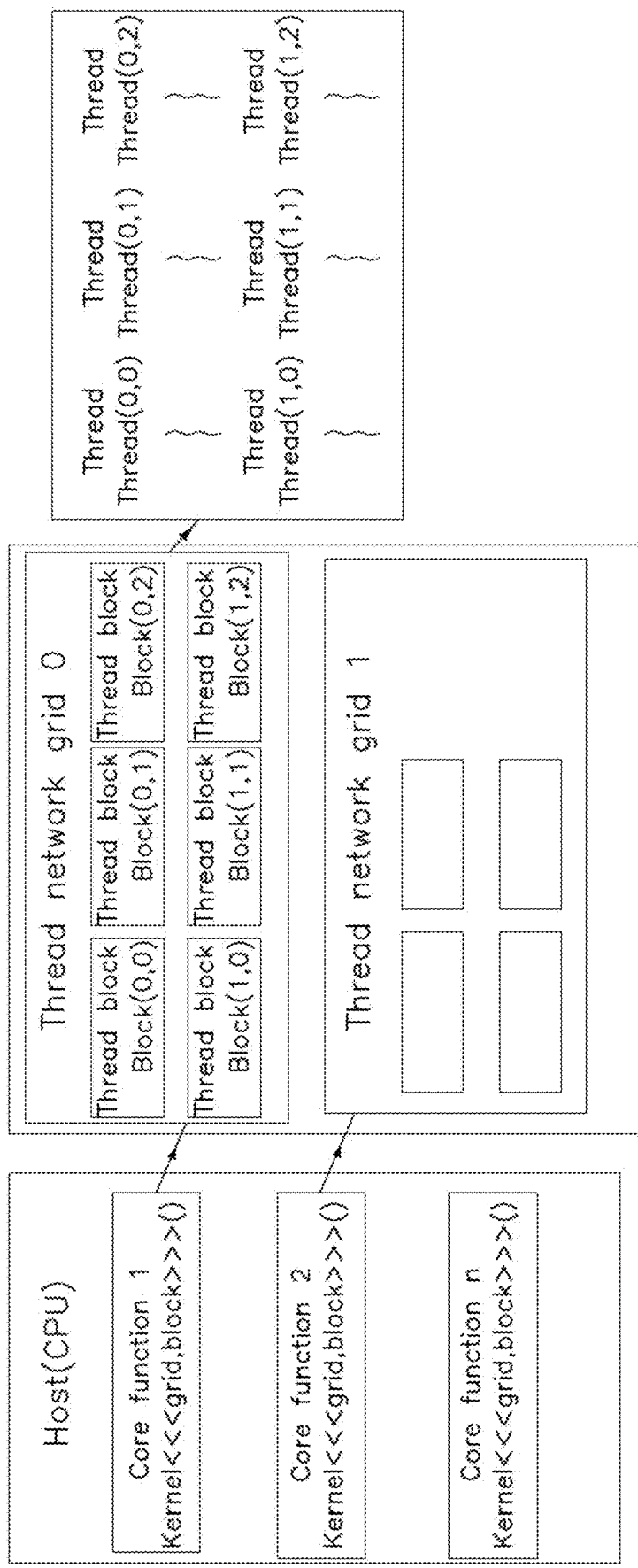
FIG. 8 is a schematic diagram of a GPU programming model.

Please refer to FIG. 8. FIG. 8 is a schematic diagram of the GPU programming model. The fluorescence image registration method provided by the embodiment of the present disclosure may be designed based on GPU, thereby increasing A rate of the fluorescence image registration. As shown in FIG. 8, the first box from the left refers to the CPU, and the second and third boxes refer to the GPU. The host contains three core functions, namely core function 1, core function 2, and core function 3. Each running core function contains a thread network (grid), and a thread network can have a plurality of thread blocks, there can be a plurality of threads in a thread block. The thread block can be understood as coarse-grained parallelism, and the threads can be understood as fine-grained parallelism. In the fluorescence image registration method provided by the embodiment of the present disclosure, coarse-grained parallelism can make a plurality of fluorescence images and a plurality of registration points of each fluorescence image be processed in parallel, and fine-grained parallelism can make each registration point realizing pixel-level registration, calibration and other processes are done in parallel. In this embodiment, in the pixel-level registration process, 81 (9*9) thread blocks can be designed and used on the GPU, which are respectively responsible for the registration of each region. There can be 512 threads in each thread block, which are respectively responsible for the accumulation of pixels in the first direction and the second direction, and finally obtain the trough position in each direction. The design idea of using thread blocks and the number of threads in the subsequent fluorescence image registration is consistent with this, and will not be described in detail.

The above is a detailed description of the method provided by the embodiment of the present disclosure. The following describes the gene sequencing instrument provided by the embodiment of the present disclosure.

An embodiment of the present disclosure also provides a gene sequencing instrument, including a storage device, at least one processor, and a computer program stored in the storage device and can be executed by the processor. When the program is executed by the processor, the block of the fluorescence image registration method is realized. It should be noted that the gene sequencing instrument may include a chip platform, an optical system, and a liquid path system. Wherein, the chip platform can be used to load biochips, the optical system can be used to acquire fluorescence images, and the liquid path system can be used to perform biochemical reactions using preset reagent.

Figure 9:
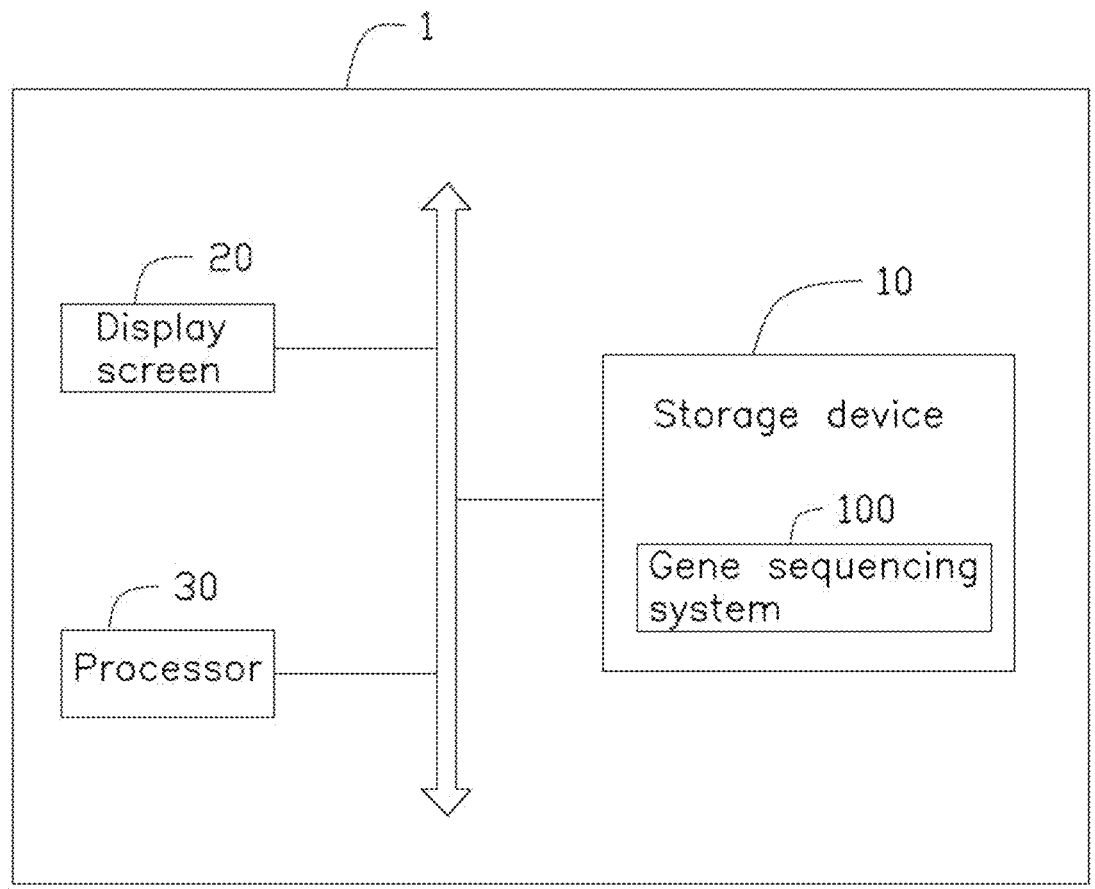
FIG. 9 is a schematic structural diagram of a gene sequencing instrument according to an embodiment of the present disclosure.

FIG. 9 is a schematic structural diagram of a gene sequencing instrument according to an embodiment of the present disclosure. As shown in FIG. 9, the gene sequencing instrument 1 includes a storage device 10 in which a gene sequencing system 100 is stored. The gene sequencing system 100 can obtain at least one fluorescence image of a biochip; select a preset local region of the fluorescence image, the preset local region having at least one borderline frame in the first direction and the second direction, the borderline frame comprising a plurality of image points of fluorescent molecules, and the first direction being perpendicular to the second direction; acquire, in the preset local region, a position of a minimum value of a sum of brightness values of pixels in the first direction and the second direction, and acquire pixel-level registration points according to the position of the minimum value of the sum of brightness values of pixels; divide the pixel-level registration points into non-defective pixels and defective pixels according to a preset classification rule; determine whether the fluorescence image meets a preset standard according to a number of the non-defective pixels, if it is determined that the fluorescence image meets the preset standard, correcting the positions of the defective pixels according to the positions of the non-defective pixels; detect image points of the fluorescent molecules on a cross line where the pixel-level registration points are located, of the borderline frames in the first direction and the second direction, and acquire a position of a center of gravity of image points of fluorescent molecules according to a center of gravity method; fit straight lines in the first direction and the second direction respectively according to the position of the center of gravity of the image points of fluorescent molecules, a cross point of the straight line fitted in the first direction and the straight line fitted in the second direction being a sub-pixel level position of the registration point; acquiring boundary points of the fluorescence image according to the straight lines fitted in the first direction and the second direction, and calculating positions of the boundary points. The present disclosure provides a high-precision GPU parallel registration fluorescent image based on point features, which can locate and register base information images of different sequencing platforms with high accuracy and efficiency. The fluorescence image registration method provided by the embodiment of the present disclosure also determines whether the quality of the fluorescence image meets the standard by the number of non-defective pixels, and discards the fluorescence image that does not meet the standard, so it has a strong anti-impurity interference ability.

In this embodiment, the gene sequencing instrument 1 may further include a display screen 20 and a processor 30. The storage device 10 and the display screen 20 may be electrically connected to the processor 30 respectively.

The storage device 10 may be different types of storage devices for storing various types of data. For example, it can be the storage device or internal memory of the gene sequencing instrument 1, or it can be a memory card that can be connected to the gene sequencing instrument 1, such as flash memory, SM card (Smart Media Card, Smart Media Card), SD card (Secure Digital Card, Secure digital card) etc. In addition, the storage device 10 may include a high-speed random access storage device, and may also include a non-volatile storage device, such as a hard disk, a memory, a plug-in hard disk, a Smart Media Card (SMC), and a Secure Digital (SD) Card, Flash Card, at least one magnetic disk storage device, flash memory device, or other volatile solid-state storage device. The storage device 10 is used to store various types of data, for example, various types of applications installed in the gene sequencing instrument 1, and information such as data set and acquired by applying the above-mentioned fluorescence image registration method.

The display screen 20 is installed in the gene sequencing instrument 1 for displaying information.

The processor 30 is used to execute the fluorescence image registration method and various software installed in the gene sequencing instrument 1, such as an operating system and application display software. The processor 30 includes, but is not limited to, a processor (Central Processing Unit, CPU), a Micro Controller Unit (MCU), and other devices for interpreting computer instructions and processing data in computer software.

The gene sequencing system 100 may include one or more modules, and the one or more modules are stored in the storage device 10 of the gene sequencing instrument 1 and are executed by one or more processors (e.g., a processor 30) to complete the embodiment of the present disclosure. For example, referring to FIG. 10, the gene sequencing system 100 may include a fluorescence image acquisition module 101, a local region acquisition module 103, a pixel-level registration point acquisition module 105, a registration point classification module 107, an image quality judgment module 109, and a position correction module 111, a gravity center acquisition module 113, a sub-pixel level registration point acquisition module 115, and a boundary point position acquisition module 117. The module referred to in the embodiment of the present disclosure may be a program segment that completes a specified function, and is more suitable than a program to describe the execution process of software in a processor.

Figure 10:
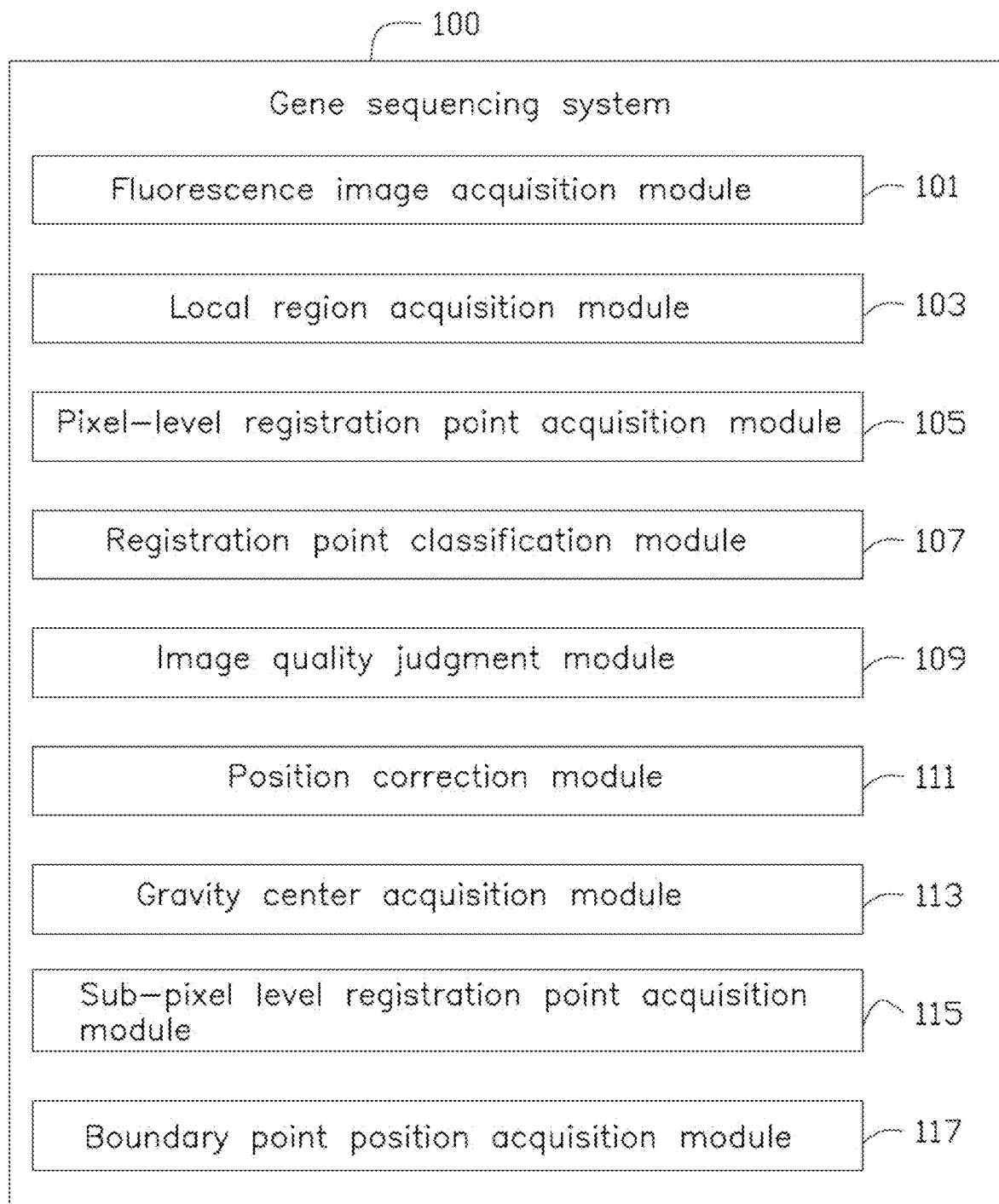
FIG. 10 is a schematic diagram of an embodiments of functional modules of the gene sequencing instrument shown in FIG. 9.

It can be understood that, corresponding to each embodiment of the above-mentioned fluorescence image registration method, the gene sequencing instrument 1 may include some or all of the functional modules shown in FIG. 10, and the functions of each module will be described in detail below. It should be noted that the same nouns and related nouns and specified explanations in the above embodiments of the fluorescence image registration method can also be applied to the following introduction to the functions of each module. To save space and avoid repetition, I won't repeat them here.

The fluorescence image acquisition module 101 can obtain at least one fluorescence image of a biochip.

The local region acquisition module 103 can select a preset local region of the fluorescence image, the preset local region having at least one borderline frame in the first direction and the second direction, the borderline frame comprising a plurality of image points of fluorescent molecules, and the first direction being perpendicular to the second direction.

The pixel-level registration point acquisition module 105 can acquire, in the preset local region, a position of a minimum value of a stun of brightness values of pixel in the first direction and the second direction, and acquire pixel-level registration point according to the position of the minimum value of the sum of brightness values of pixels.

The registration point classification module 107 can divide the pixel-level registration points into non-defective pixels and defective pixels according to a preset classification rule.

The image quality judgment module 109 can determine whether the fluorescence image meets a preset standard according to a number of the non-defective pixels.

The position correction module 111 can correct the positions of the defective pixels according to the positions of the non-defective pixels.

The gravity center acquisition module 113 can detect image points of the fluorescent molecules on a cross line where the pixel-level registration points are located, of the borderline frames in the first direction and the second direction, and acquire a position of a center of gravity of image points of fluorescent molecules according to a center of gravity method.

The sub-pixel level registration point acquisition module 115 can fit straight lines in the first direction and the second direction respectively according to the position of the center of gravity of the image points of fluorescent molecules, a cross point of the straight line fitted in the first direction and the straight line fitted in the second direction being a sub-pixel level position of the registration point.

The boundary point position acquisition module 117 can acquire boundary points of the fluorescence image according to the straight lines fitted in the first direction and the second direction, and calculate positions of the boundary points.

The embodiment of the present disclosure also provides a non-volatile computer-readable storage medium on which a computer program is stored, and when the computer program is executed by a processor, the blocks of the fluorescence image registration method in any of the above embodiments are implemented.

If the integrated module/unit of the gene sequencing system/gene sequencing instrument/computer equipment is implemented in the form of a software functional unit and sold or used as an independent product, it can be stored in a computer readable storage medium. Based on this understanding, the present disclosure implements all or part of the processes in the above-mentioned implementation methods, and can also be completed by instructing relevant hardware through a computer program. The computer program can be stored in a computer-readable storage medium. When the program is executed by the processor, it can implement the blocks of the foregoing method embodiments. Wherein, the computer program includes computer program code, and the computer program code may be in the form of source code, object code, executable file, or some intermediate forms. The computer-readable storage medium may include: any entity or device capable of carrying the computer program code, recording medium, U disk, mobile hard disk, magnetic disk, optical disk, computer memory, read-only memory (ROM), Random Access Memory (RAM), electrical carrier signal, telecommunications signal, and software distribution media.

The processor may be a central processing unit (CPU), other general-purpose processors, digital signal processors (DSP), application specified integrated circuits (ASIC), ready-made Field-Programmable Gate Array (FPGA) or other programmable logic devices, discrete gate or transistor logic devices, discrete hardware components, etc. The general-purpose processor can be a microprocessor or the processor can also be any conventional processor, etc. The processor is the control center of the gene sequencing system/gene sequencing instrument, and various interfaces and lines are used to connect the entire gene sequencing system/gene sequencing instrument.

The storage device is used to store the computer program and/or module, and the processor realizes the various functions of sequencing system/gene sequencing instrument by running or executing the computer program and/or module stored in the storage device and calling the data stored in the storage device. The storage device may mainly include a program storage area and a data storage area, where the program storage area may store an operating system, an application program required by at least one function (such as a sound playback function, an image playback function, etc.), and the like. In addition, the storage device may include high-speed random access storage device, and may also include non-volatile storage device, such as hard disks, memory, plug-in hard disks, Smart Media Card (SMC), Secure Digital (SD) cards, Flash Card, at least one magnetic disk storage device, flash memory device, or other volatile solid-state storage device.

In the several specified implementation manners provided by the present disclosure, it should be understood that the disclosed terminal and method may be implemented in other ways. For example, the system implementation described above s only illustrative. For example, the division of the modules is only a logical function division, and there may be other division methods in actual implementation.

For those skilled in the art, it is obvious that the embodiments of the present disclosure are not limited to the details of the above exemplary embodiments, and the embodiments of the present disclosure can be implemented in other specified forms without departing from the spirit or basic characteristics of the embodiments of the present disclosure, example. Therefore, from any point of view, the embodiments should be regarded as exemplary and non-limiting. The scope of the embodiments of the present disclosure is defined by the appended claims rather than the above description, and therefore it is intended to fall on All changes within the meaning and scope of equivalent elements of the claims are included in the embodiments of the present disclosure. Any reference signs in the claims should not be regarded as limiting the claims involved. Multiple units, modules or devices stated in the claims of a system, device or terminal can also be implemented by the same unit, module or device through software or hardware.

The above embodiments are only used to illustrate the technical solutions of the embodiments of the present disclosure and not to limit them. Although the embodiments of the present disclosure are described in detail with reference to the above preferred embodiments, those of ordinary skill in the neighborhood should understand that they can Modifications or equivalent replacements of the technical solutions should not depart from the spirit and scope of the technical solutions of the embodiments of the present disclosure.

What is claimed is:

1. A fluorescence image registration method applied to a gene sequencing instrument, wherein the fluorescence image registration method comprises:

obtaining at least one fluorescence image of a biochip;

selecting a preset local region of the fluorescence image, the preset local region having at least one borderline frame in a first direction and a second direction, the borderline frame comprising a plurality of image points of fluorescent molecules, and the first direction being perpendicular to the second direction;

acquiring, in the preset local region, a position of a minimum value of a stun of brightness values of pixels in the first direction and the second direction, and acquiring pixel-level registration points according to the position of the minimum value of the sum of brightness values of pixels;

dividing the pixel-level registration points into non-defective pixels and defective pixels according to a preset classification rule;

determining whether the fluorescence image meets a preset standard according to a number of the non-defective pixels;

correcting positions of the defective pixels according to positions of the non-defective pixels, if the fluorescence image meets the preset standard; and reobtaining the fluorescence image if the fluorescence image does not meet the preset standard;

detecting image points of fluorescent molecules on a cross line where the pixel-level registration points are located, of borderline frames in the first direction and the second direction, and acquiring a position of a center of gravity of image points of fluorescent molecules according to a center of gravity method;

fitting straight lines in the first direction and the second direction respectively according to the position of the center of gravity of the image points of fluorescent molecules, a cross point of the straight line fitted in the first direction and the straight line fitted in the second direction being a sub-pixel level position of the registration point;

acquiring boundary points of the fluorescence image according to the straight lines fitted in the first direction and the second direction, and calculating positions of the boundary points.

2. The fluorescence image registration method according to claim 1, wherein before obtaining the position of the minimum value of the sum of brightness values of pixels, the method further comprises:

obtaining a position of each template borderline frame in the first direction and the second direction, the template borderline frame is a template line frame preset on the biochip;

selecting a preset rectangular area according to the position of each template borderline frame; and obtaining the position of the minimum value of the sum of brightness values of pixels in the first direction and the second direction of the preset rectangular area.

3. The fluorescence image registration method according to claim 2, wherein the acquiring the position of the minimum value of the sum of brightness values of pixels in the first direction and the second direction comprises:

selecting a plurality of template lines;

respectively in the first direction and the second direction, sequentially translating the plurality of template lines in a preset rectangular area; and calculating a superimposed sum of brightness values of the pixels covered by the positions of the plurality of template lines on the preset rectangular area, the superimposed sum of the brightness values being a sum of brightness values of pixels covered by the plurality of template lines.

4. The fluorescence image registration method according to claim 1, wherein the dividing the pixel registration points into non-defective pixels and defective pixels according to the preset classification rule comprises:

obtaining pixel-level registration points on any column in the first direction of the preset local region;

calculating an absolute value of an abscissa difference between one of the pixel-level registration points and each of other pixel-level registration points on the any column; and determining that a pixel-level registration point is non-defective pixel if there are at least two of the absolute values less than a preset threshold.

5. The fluorescence image registration method according to claim 4, wherein the dividing the pixel registration points into non-defective pixels and defective pixels according to the preset classification rule further comprises:

obtaining, in the second direction of the preset local region, the pixel registration points on any row;

selecting one of the obtained pixel-level registration points, and obtaining a plurality of slopes by calculating a slope between the selected pixel-level registration point and each of other pixel-level registration points on the any row;

sorting the plurality of slopes according to a preset sorting rule, obtaining a first median value from the plurality of slopes and setting the first median value as a first slope of the selected pixel-level registration point;

obtaining a first slope of each of the other pixel-level registration points on the any row, and sorting all the first slopes of the pixel-level registration points on the any row according to the preset sorting rule, obtaining a second median value from all the first slopes and setting the second median as a second slope of the any row; and setting a point corresponding to the second slope on the any row as a reference point;

obtaining a second slope of each of other rows, and sorting the second slopes of all rows of the preset local region according to the preset sorting rule, and obtaining a third median value from all the second slopes and setting the third median value as a common slope of all rows; and performing a straight line fitting for all rows according to the common slope and the reference point, and dividing the pixel-level registration points into non-defective pixels and defective pixels according to the fitted straight line.

6. The fluorescence image registration method according to claim 5, wherein the correcting the positions of the defective pixels according to the positions of the non-defective pixels comprises:

obtaining a mean value of the abscissas of the non-defective pixels in the first direction of the preset local region, and assigning the mean value of the abscissas to the defective pixels;

obtaining, in the second direction of the preset local region, the abscissa of the defective pixel, and correcting the ordinate of the defective pixel according to the fitted straight line.

7. The fluorescence image registration method according to claim 5, wherein the acquiring the position of the center of gravity of image points of fluorescent molecules according to the center of gravity method comprises:

acquiring position coordinates of the pixel-level registration points;

acquiring brightness values of pixels of the image points of fluorescent molecules;

acquiring the position of the center of gravity of image points of the fluorescent molecules according to a preset center of gravity formula.

8. A gene sequencing instrument, comprising:

a processor; and a storage device storing one or more computer programs, which when executed by the processor, cause the processor to:

obtain at least one fluorescence image of a biochip;

select a preset local region of the fluorescence image, the preset local region having at least one borderline frame in a first direction and a second direction, the borderline frame comprising a plurality of image points of fluorescent molecules, and the first direction being perpendicular to the second direction;

acquire, in the preset local region, a position of a minimum value of a sum of brightness values of pixels in the first direction and the second direction, and acquire pixel-level registration points according to the position of the minimum value of the sum of brightness values of pixels;

divide the pixel-level registration points into non-defective pixels and defective pixels according to a preset classification rule;

determine whether the fluorescence image meets a preset standard according to a number of the non-defective pixels;

correct positions of the defective pixels according to positions of the non-defective pixels, if the fluorescence image meets the preset standard; and reobtain the fluorescence image if the fluorescence image does not meet the preset standard;

detect image points of fluorescent molecules on a cross line where the pixel-level registration points are located, of borderline frames in the first direction and the second direction, and acquiring a position of a center of gravity of image points of fluorescent molecules according to a center of gravity method;

fit straight lines in the first direction and the second direction respectively according to the position of the center of gravity of the image points of fluorescent molecules, a cross point of the straight line fitted in the first direction and the straight line fitted in the second direction being a sub-pixel level position of the registration point; and acquire boundary points of the fluorescence image according to the straight lines fitted in the first direction and the second direction, and calculate positions of the boundary points.

9. A non-transitory storage medium with a computer program stored thereon, wherein the computer program is executed by a processor of a gene sequencing instrument, the processor is configured perform a fluorescence image registration method, wherein the method comprises:

obtaining at least one fluorescence image of a biochip;

selecting a preset local region of the fluorescence image, the preset local region having at least one borderline frame in a first direction and a second direction, the borderline frame comprising a plurality of image points of fluorescent molecules, and the first direction being perpendicular to the second direction;

acquiring, in the preset local region, a position of a minimum value of a stun of brightness values of pixels in the first direction and the second direction, and acquiring pixel-level registration points according to the position of the minimum value of the sum of brightness values of pixels;

dividing the pixel-level registration points into non-defective pixels and defective pixels according to a preset classification rule;

determining whether the fluorescence image meets a preset standard according to a number of the non-defective pixels;

correcting positions of the defective pixels according to positions of the non-defective pixels, if the fluorescence image meets the preset standard; and reobtaining the fluorescence image if the fluorescence image does not meet the preset standard;

detecting image points of fluorescent molecules on a cross line where the pixel-level registration points are located, of borderline frames in the first direction and the second direction, and acquiring a position of a center of gravity of image points of fluorescent molecules according to a center of gravity method;

fitting straight lines in the first direction and the second direction respectively according to the position of the center of gravity of the image points of fluorescent molecules, a cross point of the straight line fitted in the first direction and the straight line fitted in the second direction being a sub-pixel level position of the registration point;

acquiring boundary points of the fluorescence image according to the straight lines fitted in the first direction and the second direction, and calculating positions of the boundary points.

10. The gene sequencing instrument according to claim 8, wherein before obtaining the position of the minimum value of the sum of brightness values of pixels, the at least one processor is further caused to:

obtain a position of each template borderline frame in the first direction and the second direction, the template borderline frame is a template line frame preset on the biochip;

select a preset rectangular area according to the position of each template borderline frame; and obtain the position of the minimum value of the sum of brightness values of pixels in the first direction and the second direction of the preset rectangular area.

11. The gene sequencing instrument according to claim 10, wherein the acquiring the position of the minimum value of the sum of brightness values of pixels in the first direction and the second direction comprises:

selecting a plurality of template lines;

respectively in the first direction and the second direction, sequentially translating the plurality of template lines in a preset rectangular area; and calculating a superimposed sum of brightness values of the pixels covered by the positions of the plurality of template lines on the preset rectangular area, the superimposed sum of the brightness values being a sum of brightness values of pixels covered by the plurality of template lines.

12. The gene sequencing instrument according to claim 8, wherein the dividing the pixel registration points into non-defective pixels and defective pixels according to the preset classification rule comprises:

obtaining pixel-level registration points on any column in the first direction of the preset local region;

calculating an absolute value of an abscissa difference between one of the pixel-level registration points and each of other pixel-level registration points on the any column; and determining that a pixel-level registration point is non-defective pixel if there are at least two of the absolute values less than a preset threshold.

13. The gene sequencing instrument according to claim 12, wherein the dividing the pixel registration points into non-defective pixels and defective pixels according to the preset classification rule further comprises:

obtaining, in the second direction of the preset local region, the pixel registration points on any row;

selecting one of the obtained pixel-level registration points, and obtaining a plurality of slopes by calculating a slope between the selected pixel-level registration point and each of other pixel-level registration points on the any row;

sorting the plurality of slopes according to a preset sorting rule, obtaining a first median value from the plurality of slopes and setting the first median value as a first slope of the selected pixel-level registration point;

obtaining a first slope of each of the other pixel-level registration points on the any row, and sorting all the first slopes of the pixel-level registration points on the any row according to the preset sorting rule, obtaining a second median value from all the first slopes and setting the second median as a second slope of the any row; and setting a point corresponding to the second slope on the any row as a reference point;

obtaining a second slope of each of other rows, and sorting the second slopes of all rows of the preset local region according to the preset sorting rule, and obtaining a third median value from all the second slopes and setting the third median value as a common slope of all rows; and performing a straight line fitting for all rows according to the common slope and the reference point, and dividing the pixel-level registration points into non-defective pixels and defective pixels according to the fitted straight line.

14. The gene sequencing instrument according to claim 13, wherein the correcting the positions of the defective pixels according to the positions of the non-defective pixels comprises:

obtaining a mean value of the abscissas of the non-defective pixels in the first direction of the preset local region, and assigning the mean value of the abscissas to the defective pixels;

obtaining, in the second direction of the preset local region, the abscissa of the defective pixel, and correcting the ordinate of the defective pixel according to the fitted straight line.

15. The gene sequencing instrument according to claim 14, wherein the acquiring the position of the center of gravity of image points of fluorescent molecules according to the center of gravity method comprises:

acquiring position coordinates of the pixel-level registration points;

acquiring brightness values of pixels of the image points of fluorescent molecules;

acquiring the position of the center of gravity of image points of the fluorescent molecules according to a preset center of gravity formula.

* * * * *